United States Patent [19]
Lillard, Jr.

[11] Patent Number: 6,153,182
[45] Date of Patent: Nov. 28, 2000

[54] LYMPHOTACTIN AS AN ADJUVANT

[75] Inventor: James W. Lillard, Jr., Birmingham, Ala.

[73] Assignee: UAB Research Foundation, Birmingham, Ala.

[21] Appl. No.: 09/213,878

[22] Filed: Dec. 17, 1998

Related U.S. Application Data

[60] Provisional application No. 60/068,364, Dec. 19, 1997.

[51] Int. Cl.$^7$ ..................................... A61K 38/19
[52] U.S. Cl. .................. 424/85.1; 514/2; 514/8; 514/12; 514/885
[58] Field of Search ............................ 514/2, 8, 12, 885; 424/85.1

[56] References Cited

U.S. PATENT DOCUMENTS 5,985,580  11/1999  Kelner et al. ............................ 435/7.1

*Primary Examiner*—Prema Mertz
*Attorney, Agent, or Firm*—Glenna Hendricks

[57] ABSTRACT

Compositions of lymphotactin in cellular immune enhancing amounts may advantageously be administered at very low levels in conjunction with vaccines to provide improved immune response, Suggested dosage such as 1 to 10 ηg in small animals and from 10 μg to 10 mg in large mammals may be administered.

6 Claims, No Drawings

LYMPHOTACTIN AS AN ADJUVANT

APPLICATION FOR LETTERS PATENT

This application takes priority from Provisional Patent Application 60/068,364 filed Dec. 19, 1997.

FIELD OF THE INVENTION

This invention relates to use of lymphotactin as an adjuvant to boost immune response.

BACKGROUND OF THE INVENTION

The immune response mechanism involves both systemic and localized mucosal responses to pathogens and to vaccines. The response to the immunogen or pathogen may be cell-mediated or humoral. (See *Fundamental Immunology*, 3rd. edition, (W. E. Paul, Editor), Raven Press, New York, (1993).) For example, many intestinal pathogens require a mucosal immune response to provide effective protection from illness.

The use of an adjuvant as a means of enhancing responses to immunogens has been long known. Adjuvants may function in several ways. Some act on the immune system to elicit a more effective antibody reaction to the antigen by activating host macrophages, dendritic cells, B cells and T cells, or enhancing antigen presentation. Adjuvants may enhance immune responses by prolonging the release of antigen, increasing antigen uptake, up-regulating antigen processing, stimulating cytokine release, stimulating B cell switching and maturation and/or eliminating immunosuppressor cells. Presently known adjuvants include, aluminum hydroxide and Freund's complete adjuvant. A list of the most effective adjuvants would include bacterial toxins which may be administered with the target immunogen. Sometimes these immune response-enhancing molecules are bound to the toxin. However, many of these adjuvants cause serious untoward effects.

U.S. Pat. No. 5,571,515 discloses the use of IL-12 as an adjuvant for use to enhance cell-mediated immunity.

There are four classes of chemokines: CC, C×C, C and C×3 C. Lymphotactin of the C class of chemokines is similar to CC and C×C chemokine families that are common in mammals and that are chemotactic for lymphocytes.

In the adult human, the mucosal surface encompasses more than 300 m$^2$ and requires a significant number of lymphoid cells such as the τδT cell receptor (τδTCR) intraepithelial lymphocytes (IELs), which produce lymphotactin and B cells, which produce secretory immunoglobulin (S-Ig) A antibodies (Abs). S-IgA Abs in the mucosa represent the first line of defense against invading pathogens or toxins that, if left unaltered, lead to pathology. Unfortunately, in the context of vaccine development, attempts to induce these protective Abs has not met with great success.

SUMMARY OF THE INVENTION

This invention provides means of enhancing immune response, particularly mucosal immune response, by administration of an immune-enhancing effective amount of lymphotactin in a pharmaceutically acceptable carrier. Lymphotactin may be delivered to the mucosa in conjunction with antigen. Mucosal means of application include oral, intranasal, ocular, intravaginal and/or intraurethral administration in liquid or particulate form.

DETAILED DESCRIPTION OF THE INVENTION

Lymphotactin has been known to be predominately produced by NK and CD8$^+$ cells as well as in τδT cell receptor (TCR) intraepithelial lymphocytes (IELs). The τδT cells of splenic origin do not produce lymphotactin to the same degree as similar and more abundant lymphocytes of mucosal origin, such as those of the upper and lower respiratory, gastrointestinal and reproductive tracts. Lymphotactin used in the examples was obtained from DNAX Research Institute. Lymphotactin produced by recombinant technology may be purchased from Research Diagnostics, Inc, Flanders, N.J.

Lymphotactin is particularly effective in enhancing immune responses. While bacterial toxins can boost S-IgA, these substrates have deleterious side effects in humans and other mammals. Fortunately, it is now possible, by using lymphotactin in accord with the teachings herein, to induce significant and protective Antigen-Specific S-IgA Abs in mucosal secretions. Furthermore, the strategy disclosed herein initiates serum IgA, IgM and IgG with mixed T helper type 1 and 2 (Th1/Th2) responses. Comparative humoral and cell mediated immune responses have been shown to protect laboratory animals against lethal doses of mucosal and systemic pathogens and toxins.

C chemokines such as lymphotactin can be used as a adjuvants in systemic and local, particularly mucosal, vaccine preparations. These protein-based vaccines can facilitate mucosal and systemic immunity to immunogens whether given in compositions containing in combination the C chemokine and the target antigen or administered separately to enhance immune response to the antigen.

The best known of the effective mucosal vaccines is the Salk polio vaccine. Several antigens are also available to raise immune response to intestinal diseases such as diarrhea arising from *E. coli* or Shipella species. In all of these and similar instances, the use of lymphotactin to enhance immune response would be appropriate.

Materials and Methods

Immunizations

All mice used were 8 to 10 week old C57BL/6 mice (Charles River Laboratories, Willmington, Mass.) housed in laminar cabinets. The mice were free of microbial pathogens, as determined by routine histological analysis. Mice were intranasally immunized with 10 $\mu$l (5 $\mu$l per nostril) of sterile phosphate buffered saline (PBS), pH 7.5 containing 25 $\mu$g chicken egg albumin (OVA from Sigma Chemical Col, St. Louis, Mo.) alone (no lymphotactin) or with 0.01, 0.1, 1.0 or 5 $\mu$g of murine lymphotactin on days 0, 7 and 14.

Sample Collection

Serum samples were collected via retro-orbital puncture using sterile heparinized capillary tubes. Vaginal secretion samples were obtained by flushing the vaginal cavity with 50 $\mu$l PBS three times for a total volume equal to about 150 $\mu$l. Fecal pellets were collected, weighed and dissolved in PBS containing 0.1% sodium azide (100 mg fecal pellet per 1 ml PBS/sodium azide). These samples were vortexed, centrifuged and the supernatants were collected for analysis. These mucosal and serum samples were accumulated at weekly intervals and analyzed for antigen (e.g., OVA)-specific IgA, IgM, IgG, IgE, IgG1, IgG2a, IgG2b and IgG3 antibody titers. Mice were sacrificed on day 21 for analysis of OVA-specific antibody forming cells and T cell proliferative and cytokine profile responses.

Cell Preparation

Submandibular and cervical lymph nodes (SM/CLN), mesenteric lymph nodes (MLN), Peyer's patches (PP), vaginal ileal lymph nodes (ILN) and spleen (SP) suspensions were made by passage of tissue through wire mesh. After the excision of PPs, the small intestine was isolated to determine the Ig secreting cells in the intestinal tract which directly relates to protection against intestinal pathogens. The intestinal tissue was then gently cleaned, minced and treated with 1 mM EDTA in PBS at 37° C. with agitation for 15 to 30 minutes. Next, these tissues were treated with collagenase in RPMI media for approximately 1 hour. Finally, lamina propria lymphocytes (LPL) were isolated using a percoll (Pharmacia, Uppsala, Sweden) gradient.

The lower respiratory tract (lung) and salivary gland (SG) tissues were isolated, cleaned, minced and washed in PBS. These tissues were also digested with collagenase, isolated and examined to determine the antigen-specific Ig secreting cells and T cell-mediated immunity in the lung and salivary glands, which are important for lower and upper respiratory immunity.

The nasal tract and nasopharyngeal-associated lymphoid tissue (NALT) was isolated and passed over sterile glass fiber to acquire a single cell suspension of lymphocytes. The nasal tract and NALT were studied to determine the number of Ig secreting cells in the upper respiratory tract needed for protection against respiratory pathogens and toxins.

Antigen-Specific Antibody Titer Detection by ELISA and ELISPOT Assays

Antibody titers in sera and secretions were analyzed by ELISA to confirm the source of antigen-specific antibodies detected by ELISA, quantitation of vaccine antigen-specific antibody spot forming cells from the SP, PP, MLN, SM/CLN, lung and NALT were enumerated by ELISPOT analysis.

Enumeration of Antigen-Specific T Cell Proliferative Responses

T cell depleted irradiated (3,000 rads) spleen cells from naive mice were used as feeder cells for T cell proliferation assays. T cells from the SM/CLN, MLN, PP, lung, ILN and SP of immunized mice were purified using a nylon wool column. (Purified T cells ($2.5 \times 10^5$ cells/ml) were cultured with or without 0.5 mg/ml OVA plus feeder cells ($0.5 \times 10^6$ cells/ml) in complete RPMI media in round bottom tissue culture treated 96well plates. Cells were incubated at 37° in 5% $CO_2$. After 48 hours of incubation, 10 $\mu$l of 50 $\mu$Ci/ml [methyl-$^3$H]-thymidine was added to each well. Proliferation or thymidine uptake was measured 18 hours later. The stimulation index of the various samples was determined and expressed as the counts per minutes (CPM) of cultures containing OVA divided by the CPMs of cultures lacking OVA.

CD4 T cells that had been isolated using a mouse CD4 isolation column were also studied.

RESULTS

The administration of lymphotactin in conjunction with vaccine resulted in increased IgA, IgG, (IgG1, IgG2a, IgG2b, IgG3) and IgM titers in the serum. Increase in fecal IgA and IgG and vaginal IgA and IgG was also found. Additionally, augmentation of antigen-specific T cell proliferation of immunized mice was also observed in lymphocytes isolated from SM/CLN, MLN, PP, spleen, lung and ILN. Antibody spot forming cells from NALT, SP, PP, MLN, lung and SM/CLN were shown to secrete antigen-specific IgA, IgM and IgG antibodies. Hence, it can be seen that the immune responses were increased by exposure of the mucosa to lymphotactin.

Compositions of lymphotactin in cellular immune enhancing amounts may advantageously be administered at very low levels in conjunction with vaccines. Suggested dosage such as 1 to 10 ηg in small animals and from 10 $\mu$g to 10 mg in large mammals may be administered. Lymphotactin may be administered in the usual pharmaceutical carriers such as saline, buffered saline, glucose, etc. Lymphotactin may be administered to the mucosa in any manner. Preferred methods of administration involve direct application to the mucus membranes. Such compositions may, for example, be provided in the form of drops, such as nose, ear or eye drops or in sprays. Dry preparations such as lyophilized lymphotactin with powdered carriers may, for example, be inhaled or sprayed on the mucosa. Such compositions may also be provided in capsules or in tablet form for ingestion. The lymphotactin may also be administered on a solid support such as a sponge or fiber material. Such administration is particularly valuable for use in environments where access to sterile equipment is limited. Compositions for oral ingestion may be enteric coated. The adjuvants may, additionally, be added to liquids or solids for administration by mouth. For example, the adjuvants of the invention may be administered in feed or water or on solid supports such as sponges and fabrics. For example, the adjuvants may be administered in or on baits.

The adjuvants may be given orally in alkaline solutions containing antigens appropriate for raising antibodies against organisms which give rise to intestinal diseases to raise mucosal antibodies. Alkaline solutions such as those containing bicarbonates protect antigens and adjuvants from destruction in the upper GI tract.

What is claimed is:

1. A method of enhancing an immune response by administering an immune-enhancing effective amount of lymphotactin in a pharmaceutically acceptable carrier.

2. A method of claim 1 wherein the lymphotactin is administered directly to the mucosa.

3. A method of claim 2 wherein the lymphotactin is administered in the form of drops or a spray.

4. A method of claim 2 wherein the lymphotactin is administered in powder form.

5. A method of claim 1 wherein the lymphotactin is on a solid support.

6. A method of claim 1 wherein the lymphotactin is administered orally.

* * * * *